United States Patent
Chornenky et al.

(10) Patent No.: US 8,251,986 B2
(45) Date of Patent: Aug. 28, 2012

(54) METHOD OF DESTROYING TISSUE CELLS BY ELETROPORATION

(75) Inventors: Victor I. Chornenky, Minnetonka, MN (US); Ali Jaafar, Eden Prairie, MN (US)

(73) Assignee: AngioDynamics, Inc., Latham, NY (US)

( * ) Notice: Subject to any disclaimer, the term of this patent is extended or adjusted under 35 U.S.C. 154(b) by 411 days.

(21) Appl. No.: 12/501,225

(22) Filed: Jul. 10, 2009

(65) Prior Publication Data

US 2011/0009860 A1 Jan. 13, 2011

Related U.S. Application Data

(63) Continuation of application No. 11/106,835, filed on Apr. 15, 2005, now Pat. No. 7,938,824, which is a continuation of application No. 09/931,672, filed on Aug. 17, 2001, now Pat. No. 6,892,099.

(60) Provisional application No. 60/267,106, filed on Feb. 8, 2001, provisional application No. 60/225,775, filed on Aug. 17, 2000.

(51) Int. Cl.
*A61B 18/18* (2006.01)

(52) U.S. Cl. ............... 606/32; 606/41; 607/2; 607/115; 435/173.6

(58) Field of Classification Search .............. 606/20–41, 606/42; 607/2, 3, 72, 101, 102, 115, 116; 604/20–22; 435/461, 173.6, 285.2
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |

(Continued)

FOREIGN PATENT DOCUMENTS

DE 863111 1/1953

(Continued)

OTHER PUBLICATIONS

Mazurek, at al., Effect of Short HV Pulses on Bacteria and Fungi: IEEE Transactions on Dielectric and Electrical Insulation, vol. 2 No. 3, Jun. 1995, p. 418-425.*

(Continued)

*Primary Examiner* — Michael Peffley
*Assistant Examiner* — Khadijeh Vahdat
(74) *Attorney, Agent, or Firm* — Harry K. Ahn; McCarter & English, LLP

(57) ABSTRACT

An apparatus and method for performing non-invasive treatment of the human face and body by electroporation in lieu of cosmetic surgery is provided. The apparatus comprises a high voltage pulse generator and an applicator having two or more electrodes in close mechanical and electrical contact with the patient's skin for applying the pulses to the patient's skin. The applicator may consist of two pieces with one electrode having a sharp tip and another having a flat surface. High voltage pulses delivered to the electrodes create at the tip of the sharp electrode an electric field high enough to cause death of relatively large subcutaneous fat cells by electroporation. Moving the electrode tip along the skin creates a line of necrotic subcutaneous fat cells, which later are metabolized by the body. Multiple applications of the electrode along predetermined lines on the face or neck create shrinkage of the skin and the subcutaneous fat volume underlying the treated area.

21 Claims, 6 Drawing Sheets

U.S. PATENT DOCUMENTS

| | | |
|---|---|---|
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,944,710 A * | 8/1999 | Dev et al. ............... 604/500 |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Hofmann et al. |
| 6,085,115 A | 7/2000 | Weaver et al. |
| 6,090,106 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 2001/0039393 A1* | 11/2001 | Mori et al. ............... 604/22 |
| 2001/0044596 A1 | 11/2001 | Jaafar |
| 2002/0010491 A1 | 1/2002 | Schoenbach |
| 2002/0040204 A1* | 4/2002 | Dev et al. ............... 604/20 |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0143365 A1* | 10/2002 | Herbst ............... 607/2 |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088199 A1 | 5/2003 | Kawaji |
| 2003/0130711 A1 | 7/2003 | Pearson et al. |
| 2003/0170898 A1 | 9/2003 | Gundersen et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0243107 A1 | 12/2004 | Mackoviak et al. |
| 2004/0267189 A1 | 12/2004 | Mavor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0043345 A1 | 2/2007 | Davalos et al. |
| 2007/0118069 A1 | 5/2007 | Persson et al. |
| 2008/0052786 A1 | 2/2008 | Lin et al. |

FOREIGN PATENT DOCUMENTS

| | | |
|---|---|---|
| DE | 4000893 | 7/1991 |
| EP | 0378132 | 7/1990 |
| EP | 0935482 | 5/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |

OTHER PUBLICATIONS

Lurquin, Paul, Gene Transfer by Electroporation: Molecular Biotechnology, vol. 7, 1997, p. 5-35.*

Amasha, et al., Quantitative Assessment of Impedance Tomography for Temperature Measurements in Microwave Hyperthermia, *Clin. Phys. Physiol. Meas.*, 1998, Suppl. A, 49-53.

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Bown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, *Electrophorous electricus*," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994.

Cowley, Good News for Boomers, Newsweek, Dec. 30, 1996/Jan. 6, 1997.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005.

Davalos, et al ., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980.

Foster, R.S., et al., High-intensity focused ultrasound in the treatment of prostatic disease. *Eur. Urol.*, 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6$^{th}$ Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed. Eng.* vol. 2 2000. 157-187.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Weaver, Electroporation: A General Phenomenon for Manipulating Cells and Tissues, *Journal of Cellular Biochemistry*, 51: 426-435, 1993.

Weaver, et al., Theory of Electroporation: Aa Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

* cited by examiner

METHOD OF DESTROYING TISSUE CELLS BY ELETROPORATION

CROSS-REFERENCE TO RELATED APPLICATIONS

This is a continuation of U.S. application Ser. No. 11/106,835, filed Apr. 15, 2005, now U.S. Pat. No. 7,938,824, which is a continuation of U.S. application Ser. No. 09/931,672, filed Aug. 17, 2001, now U.S. Pat. No. 6,892,099 which has been reissued as Reissue No. 42,277, which claims priority to U.S. provisional application Ser. No. 60/267,106, filed Feb. 8, 2001 and to U.S. provisional application Ser. No. 60/225,775, filed Aug. 17, 2000, all of which are incorporated herein by reference.

FIELD OF THE INVENTION

The present invention relates generally to electroporation of tissues and, specifically, to apparatus and methods for reducing subcutaneous fat deposits, performing virtual face lifts, and body sculpturing.

BACKGROUND OF THE INVENTION

"Cosmetic surgery" is a phrase used to describe broadly surgical changes made to a human body with the usual, though not always, justification of enhancing appearance. This area of medical practice constitutes an ever-growing industry around the world. Obviously, where such a procedure fails to deliver an enhanced appearance, the procedure fails to meet the desired goal. One of the reasons that the majority of current procedures fail to deliver upon their promise is that, for the most part, current procedures are invasive, requiring incisions and suturing, and can have serious and unpleasant side effects, including but not limited to scarring, infection, and loss of sensation.

One of the more common forms of cosmetic surgery is the "face-lift." A face-lift is intended to enhance facial appearance by removing excess facial skin and tightening the remaining skin, thus removing wrinkles. A face-lift is traditionally performed by cutting and removing portions of the skin and underlying tissues on the face and neck. Two incisions are made around the ears and the skin on the face and neck is separated from the subcutaneous tissues. The skin is stretched, excess tissue and skin are removed by cutting with a scissors or scalpel, and the skin is pulled back and sutured around the ears. The tissue tightening occurs after healing of the incisions because less skin covers the same area of the face and neck and also because of the scars formed on the injured areas are contracting during the healing process.

Traditional face-lift procedures are not without potential drawbacks and side effects. One drawback of traditional cosmetic surgery is related to the use of scalpel and scissors. The use of these devices sometimes leads to significant bleeding, nerve damage, possible infection and/or lack of blood supply to some areas on the skin after operation. Discoloration of the skin, alopecia (boldness), is another possible side effect of the standard cosmetic surgery. The overall quality of the results of the surgery is also sometimes disappointing to the patients because of possible over-corrections, leading to undesired changes in the facial expression. Additionally, face-lift procedures require a long recovery period before swelling and bruising subside.

The use of lasers to improve the appearance of the skin has been also developed. Traditional laser resurfacing involves application of laser radiation to the external layer of the skin—the epidermis. Destruction of the epidermis leads to rejuvenation of the epidermis layer. The drawback of the laser resurfacing procedure is possible discoloration of the skin (red face) that can be permanent.

Another laser procedure involves using optical fibers for irradiation of the subcutaneous tissues, such as disclosed in U.S. Pat. No. Re36,903. This procedure is invasive and requires multiple surgical incisions for introduction of the optical fibers under the skin. The fibers deliver pulsed optical radiation that destroys the subcutaneous tissues as the tip of the fiber moves along predetermined lines on the face or neck. Debulking the subcutaneous fat and limited injury to the dermis along the multiple lines of the laser treatment results in contraction of the skin during the healing process, ultimately providing the face lift. The drawback of the method is its high price and possibility of infection.

Electrosurgical devices and methods utilizing high frequency electrical energy to treat a patient's skin, including resurfacing procedures and removal of pigmentation, scars, tattoos and hairs have been developed lately, such as disclosed in U.S. Pat. No. 6,264,652. The principle drawback of this technology is collateral damage to the surrounding and underlying tissues, which can lead to forming scars and skin discoloration.

Other forms of cosmetic surgery are also known. One example is liposuction, which is an invasive procedure that involves inserting a suction device under the skin and removing fat tissues. As with other invasive surgical procedures, there is always a risk of infection. In addition, because of the invasive nature of the procedure, physicians usually try to minimize the number of times the procedure must be performed and thus will remove as much fat tissue as possible during each procedure. Unfortunately, this procedure has resulted in patient deaths when too much tissue was removed. Assuming successful removal of excess fat tissue, further invasive surgery may be required to accomplish desired skin tightening.

The prior art to date, then, does not meet the desired goal of performing cosmetic surgery in a non-invasive manner while causing minimal or no scarring of the exterior surface of the skin and at the same time resulting in the skin tightening.

OBJECTS OF THE INVENTION

It is an object of the present invention to provide an apparatus and method which uses electroporation to cause necrosis of cells in the subcutaneous layer of fat and the interior side of the dermis, resulting in the contraction and tightening of the skin. In particular, it is an object of the present invention to provide method and apparatus for performing face and neck lift and others similar procedures on the face in a non-invasive manner.

Another object of the present invention is to provide an apparatus and method for significant bulk reduction of the number of subcutaneous fat cells in the body, resulting in a significant weight loss.

Still another object of the present invention is to provide non-invasive apparatus and method for cosmetic and weight loss procedures.

Still another object of the invention is to provide an apparatus and method for selective removal of fat in different areas to enable changing the shape of the body, or body sculpturing.

SUMMARY OF THE DISCLOSURE

The present invention provides an apparatus and method for creation of a controlled injury or alteration to the subcutaneous tissue and/or underside of the dermis, with the following healing process leading to the contraction of the skin; and/or to the controlled destruction of fat cells, leading to their permanent loss. In the present invention the damage to the subcutaneous tissue, underside of the dermis, and/or fat cells is caused by electroporation.

An apparatus in accord with the current invention comprises a voltage pulse generator, an applicator with two or multiple electrodes of different shapes and sizes and a cable connecting the electrodes to the pulse generator. The pulse generator produces set of high voltage pulses of predetermined amplitude, duration and number to cause necrosis in a treated area of subcutaneous tissues.

A method in accord with the current invention comprises application of electrical pulses to the electrodes positioned on the skin in a treatment area. For a face lift, flat and needle-like electrodes are used, the last one providing a strong and non-uniform electric field predominantly normal to the surface of the skin. The amplitude, duration and number of applied pulses are selected to cause necrosis of fat cells to a predetermined depth in the subcutaneous tissue and a limited necrosis of the underside of the dermis. A number of lines of predetermined pattern are exposed to electroporation. Later, during the healing process the skin on the treated area contracts. The injury to the tissues made by electroporation is very gentle and selective; it does not produce scars on the epidermis, the most external layer of the skin.

A method of weight loss and body sculpturing in accord with the present invention comprises application of electroporation pulses to a significant volume of fat tissue. In this case both electrodes are flat and attached to the arms of a forceps. The electrodes are moveable towards and away from each other and are capable of pinching skin with underlying subcutaneous fat and electroporating it. Application of flat, parallel electrodes produces a electric field is uniform in the tissue that effects only fat cells.

For weight loss a voltage generator coupled to multiple needle type electrodes may be used.

In another embodiment of the present invention, an electroporation apparatus for bulk weight loss may comprise apparatus for production of a pulsed magnetic field and its application to the area to be treated. In this embodiment of the present invention, a curl electric field for the electroporation of subcutaneous fat is created by the pulsed magnetic field. Curl electric field causes eddy currents in the tissue and at an appropriate amplitude above kills the fat cells.

BRIEF DESCRIPTION OF THE DRAWINGS

The objects and advantages of the present invention will be appreciated from the following specification when read in conjunction with the accompanying drawings wherein:

FIG. 3 is a schematic illustration of different applicators of the present apparatus wherein

DESCRIPTION OF THE PREFERRED EMBODIMENTS

Figure 1:
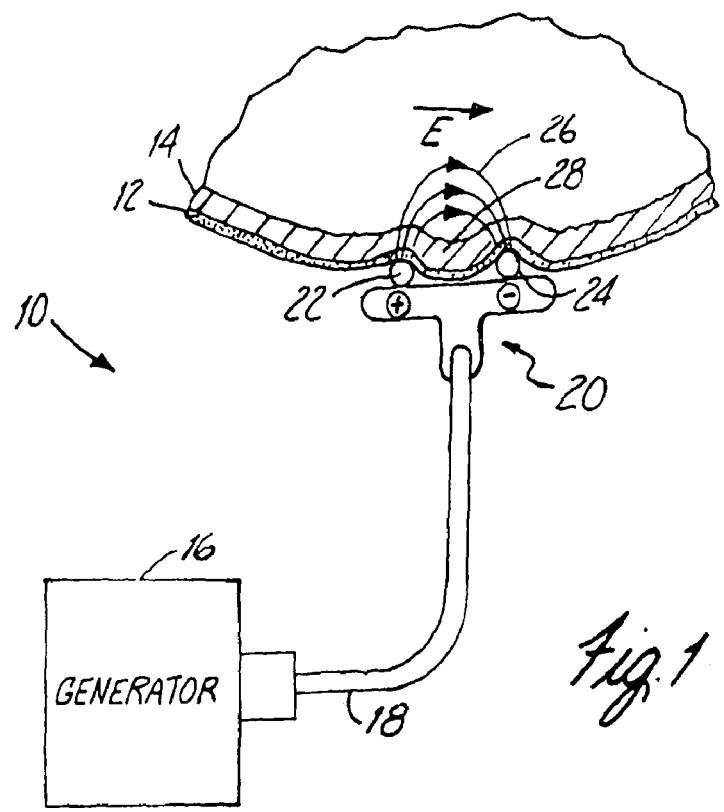
FIG. 1 is a schematic illustration of an apparatus with an applicator having an array of symmetric electrodes shown during electroporation treatment.

The term "electroporation" (EP) refers to the use of electric field pulses to induce microscopic pores in the cell membranes called "electropores". Depending on the parameters of the electric pulse, an electroporated cell can survive the pulse or die. The cause of death of an electroporated cell is believed to be a chemical imbalance, resulting from the fluid communication with the extra cellular environment through the pores. The number and size of electropores created depends on the product of the amplitude E and duration t of the pulse. Below a certain limit, no electropores are induced at all. This limit is different for different cells and depends, principally, on their sizes. The smaller the cell, the higher the product of the amplitude and duration must be to induce pores. Above the lower limit the number of pores and their effective diameter increases with the product Et. Until an upper limit is achieved, cells survive pulsing and restore their viability thereafter. Above the upper limit the pores diameters and number become too large for a cell to survive. It cannot repair itself by any spontaneous or biological process and dies. As noted, a cell's vulnerability to an electric field depends on its size: the larger the cell, the lower the electric field required for killing it. If cells of different sizes are exposed to the same electric field, the largest cells are the first to die. Thus, application of an electric field having preselected parameters can result in selectively killing particular cells.

A desirable target for cell death using the present invention is adipose tissue, commonly called fat. Adipose cells do not proliferate in adults. Their number is fixed at a very early age. Adipose cells can change their size by accumulating or loosing lipids and be responsible for significant, up to two-fold increase in the body weight. Cutting down in the number of large adipose cells results in a significant weight loss in the fat tissue and the whole body. If fat cells are destroyed by any means, their content is metabolized by the body, i.e., scavenged by macrophages, and their number is not restored. The loss of adipose cells, then, is permanent.

Adipose tissue consists of lipid-filled cells ranging in size from 25 to 200 microns. An applied electric field affects the various sized cells differently as previously mentioned. For example, if an electric field, equal to the upper electroporation limit for 100 micron cells (about 10-20 V/mm) is applied to a fat tissue, all cells with sizes from 100 micron and above, will die. The dead cells will be disposed later by macrophages, and the body will metabolize the lipids stored in these cells. Small adipose cells, for which the applied electric field is below the upper electroporation limit, survive any number of electric pulses without any morphological or functional damage.

Pulsed electric fields can be applied to fat deposits inside the body by different methods. In a first method two electrodes are applied to the skin over the fat tissue at some distance from each other and electric microsecond pulses are applied by the electrodes to the tissue. The pulse electric field, created by these two electrodes is non-uniform; it is higher near the electrodes and decreases with the depth. The electric field at the fat deposits should reach several tens of volts per mm to be able to kill adipose cells of large diameters. At the skin level the non-uniform electric field will be significantly higher. To be harmless for the skin cells, the field should not exceed the value of the upper electroporation limit for skin cells. The cells in the epidermic basal layer of the skin, which is responsible for the mitotic division and continuous rejuvenation of the skin, have dimensions of about 10 microns or less (6-10 microns). This is 10 or more times less than that of the targeted adipose cells, which is about 100 microns and larger as noted earlier. The upper electroporation limit for the skin cells in accordance with their size is therefore about 10 times higher than that of adipose cells of 100 microns diameter.

A second method of applying an electric field to the subcutaneous adipose tissue or the skin is by applying short magnetic pulses preferentially normally to the skin. The transient magnetic field creates curl electric field in the skin and the underlying tissues. This curl electric field causes eddy currents in the cells. If the magnitude of this transient electric field reaches the upper electroporation limit for the cells, it will kill them exactly as does the potential electric field created by charged electrodes.

The depth of penetration of the electric field in the skin and the fat tissue under it depends on the distance between the electrodes, their shape and size. The larger the size of electrodes and the distance between them, the deeper the penetration will be. If the electrodes are small enough and the distance between them is short, the electric field penetrates only into the skin and does not reach the underlying tissues.

If pulsed electric field penetrates only in the skin and its amplitude is high enough to kill skin cells (several hundred volts per mm), electroporation can be used for selective cell killing. The dead cells are removed by macrophages and the skin shrinks during the healing process. This skin shrinkage can be planned in advance both in terms of directions and degree. By selecting a number, direction and length of the electroporation "cuts" the operator can control the future shrinks. This method can be used for correcting wrinkles and skin pouches on the face, the neck, and on the upper and lower eye lids.

The skin electroporation treatment together with fat reducing electroporation treatment can be used as alternative to cosmetic surgery for the face lift, the upper and lower eye lid surgery, the forehead lift and body sculpturing practically in all parts of the human body.

An electroporation treatment presents several notable advantages over present cosmetic surgery procedures. First, an electroporation treatment is sterile. The most upper layer of the skin, comprising horny dead cells, is very resistant to any damage from an electroporation treatment; it protects the lower layers of the skin from infection.

The electroporation virtual facelift and body sculpturing can be performed in step by step fashion in a multi-session process. This method allows taking into account actual results of previous sessions and directs process of reshaping of the face or body to desired objectives. The treatment can be performed by a medical professional or by the patient him/herself.

With the foregoing generalized explanation of the present invention, apparatus in accord therewith may be described. Referring to FIG. 1, an electroporation system 10 in accord with the invention is schematically shown with a cross section of a piece of skin 12 with subcutaneous tissue 14 during electroporation treatment. Electroporation system 10 includes a power supply 16 for generating high voltage pulses that are sent though an appropriate electrical connector 18 to an applicator 20. Applicator 20 includes electrodes 22 and 24 that engage skin 12 and will be appropriately insulated to ensure safe handling. Additionally, the applicator will preferably be configured so as to ensure ease of handling, and thus could take many forms. The electrodes 22 and 24 may take the form of needle electrodes. The electric field created between the electrodes 22 and 24 is depicted with field lines 26 and is applied to the skin 12 and subcutaneous tissue or fat 14. In the areas close to the electrodes the electric field has an amplitude exceeding the upper electroporation limit, thus causing death to fat cells. This area of fat cell necrosis is indicated at 28.

Figure 2:
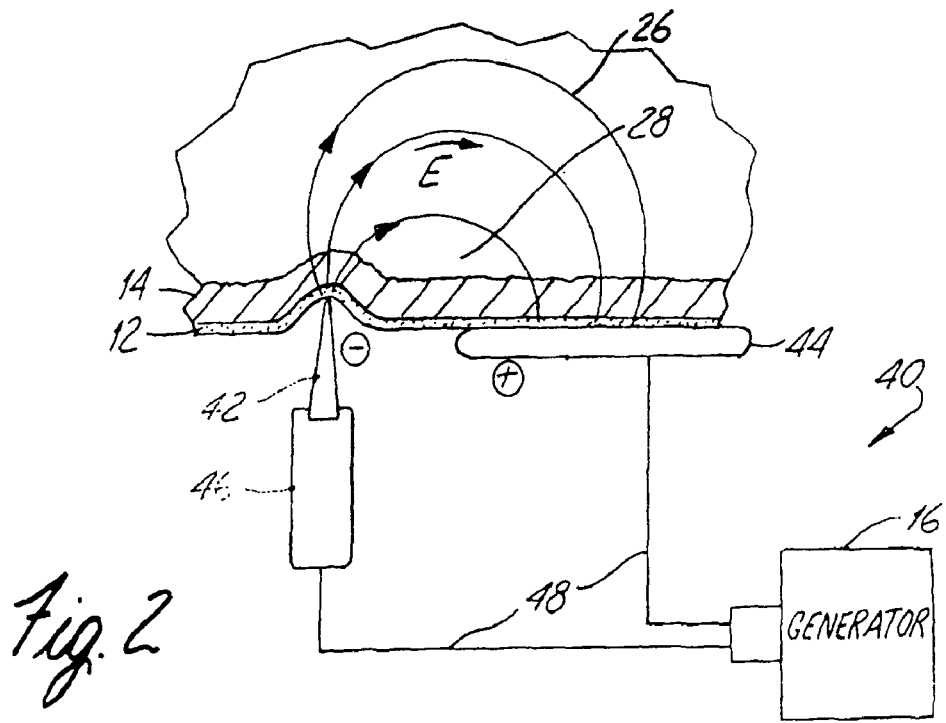
FIG. 2 is a schematic illustration of an apparatus with an applicator having one flat electrode and one a needle like electrode shown during electroporation treatment.

In FIG. 2 an alternative embodiment 40 of the present invention is shown with an applicator having two members: a needle-like electrode 42 and a flat electrode 44. If desired, the system 40 may include an insulating handle 46 configured to be held by an operator to facilitate the manual manipulation of the electrode 42. The high voltage pulse power supply 16 is connected to the applicator electrodes 42 and 44 by appropriate electrical connectors 48. Both electrodes 42 and 44 are engaged with skin 12. Electric field lines 26 depict an electric field between the electrodes 42 and 44. The area 28, where the electric field is the highest, is the treatment area where the amplitude of the electric field exceeds the upper electroporation limit and causes cell death.

Figure 3C:
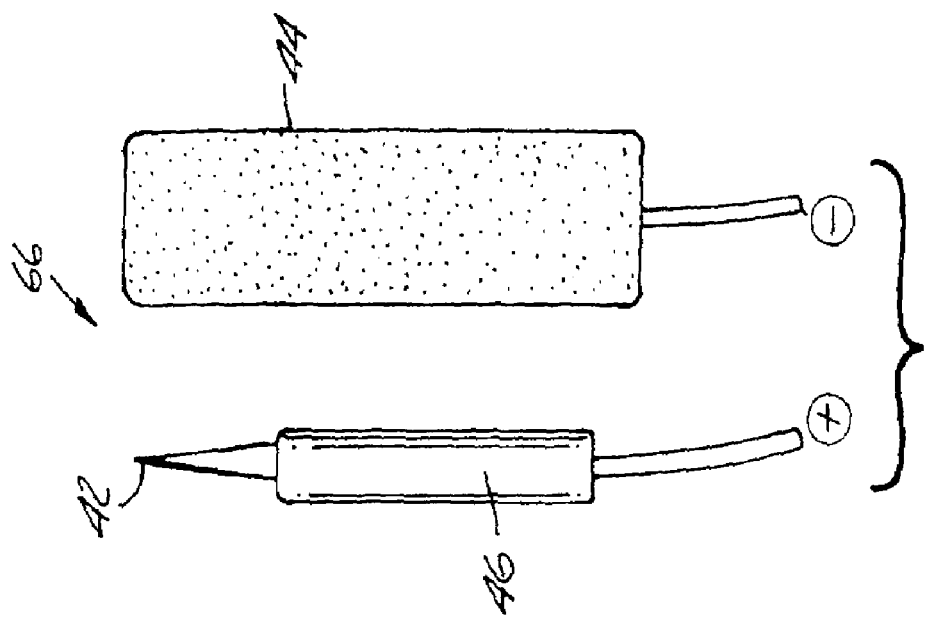
FIG. 3c illustrates applicator having one flat electrode and one needle like electrode.
Figure 3B:
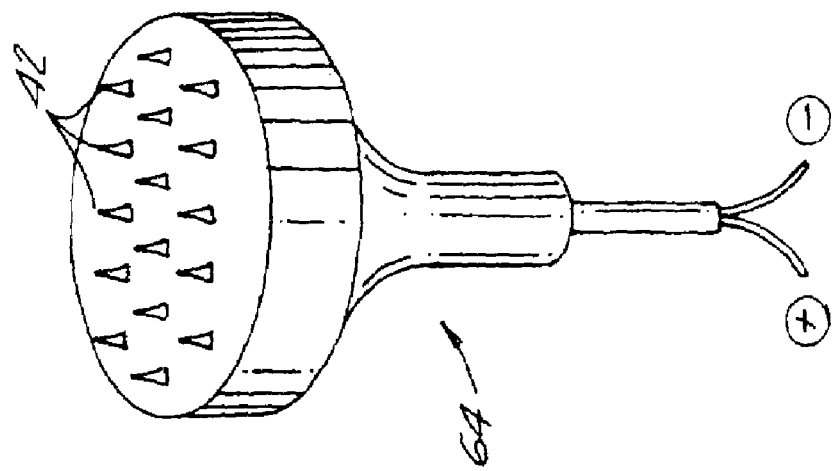
FIG. 3b illustrates an applicator having an array of needle like electrodes.
Figure 3A:
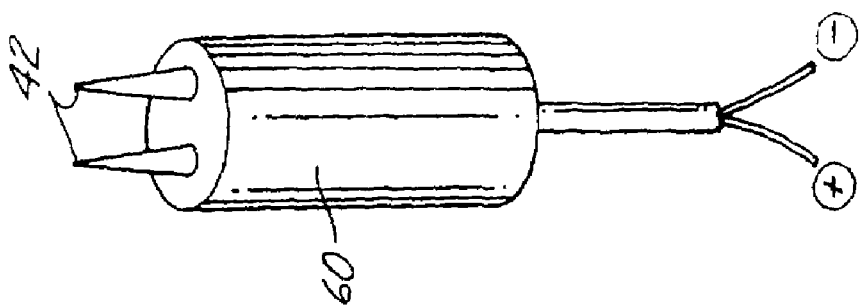
FIG. 3a illustrates an applicator with two needle like electrodes.

In FIG. 3 different versions of applicators are schematically shown. FIG. 3a illustrates an applicator 60 with two needle-like electrodes 64. FIG. 3b shows an applicator 64 with an array of needle-like electrodes 64. FIG. 3c depicts an applicator 66 like that shown in FIG. 2 and comprising a needle-like electrode 42 and a flat electrode such as electrode 44.

Figure 4B:
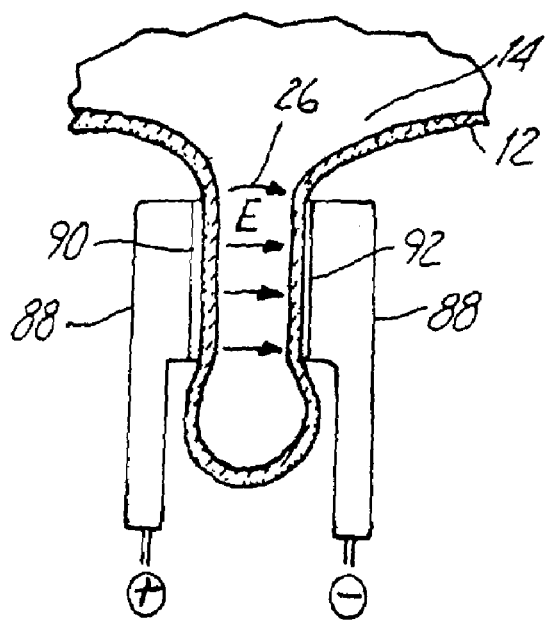
FIG. 4b is a schematic illustration of the forceps flat electrodes in closed position shown during electroporation treatment.
Figure 4A:
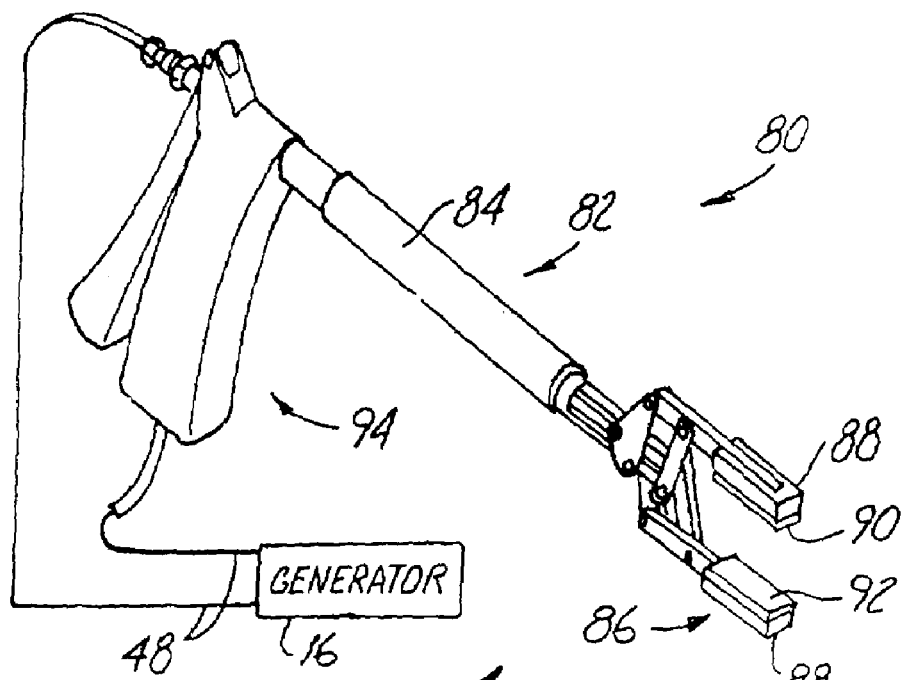
FIG. 4a is a perspective view of a forceps type applicator with two flat electrodes in an open position.

FIGS. 4a and 4b illustrate another embodiment 80 of an electroporation system in accord with the present invention useful for bulk fat reduction. System 80 includes an applicator 82 comprising a body or support member 84 supporting calipers or forceps apparatus 86. The calipers apparatus 86 includes a pair of pivotable arms 88 mounted at the distal end thereof. The arms 88 support a pair of electrodes 90 and 92. Applicator 82 may include a pistol grip 94 mounted on a proximal end of the elongated tubular support member 84 for enabling ease of manipulation of same. The electrodes 90 and 92 are mounted on a moveable linkage so that the electrodes are moveable toward and away from each other. A power supply 16 and electrical connectors 48 are also included within a system 80 to provide pulse electrical power to the electrodes 90 and 92.

FIG. 4b schematically illustrates an electroporation treatment utilizing system 80. As shown in the figure, a "fold" of skin 12 with underlying subcutaneous tissue—fat—14 is compressed between arms 88 and thus electrodes 90 and 92. A uniform electric field 26 is applied to the skin 12 and subcutaneous tissue 14 clamped between electrodes. Only the large fat cells are killed in this field configuration because the cells of the dermis are spared death because of their small size.

Figure 5:
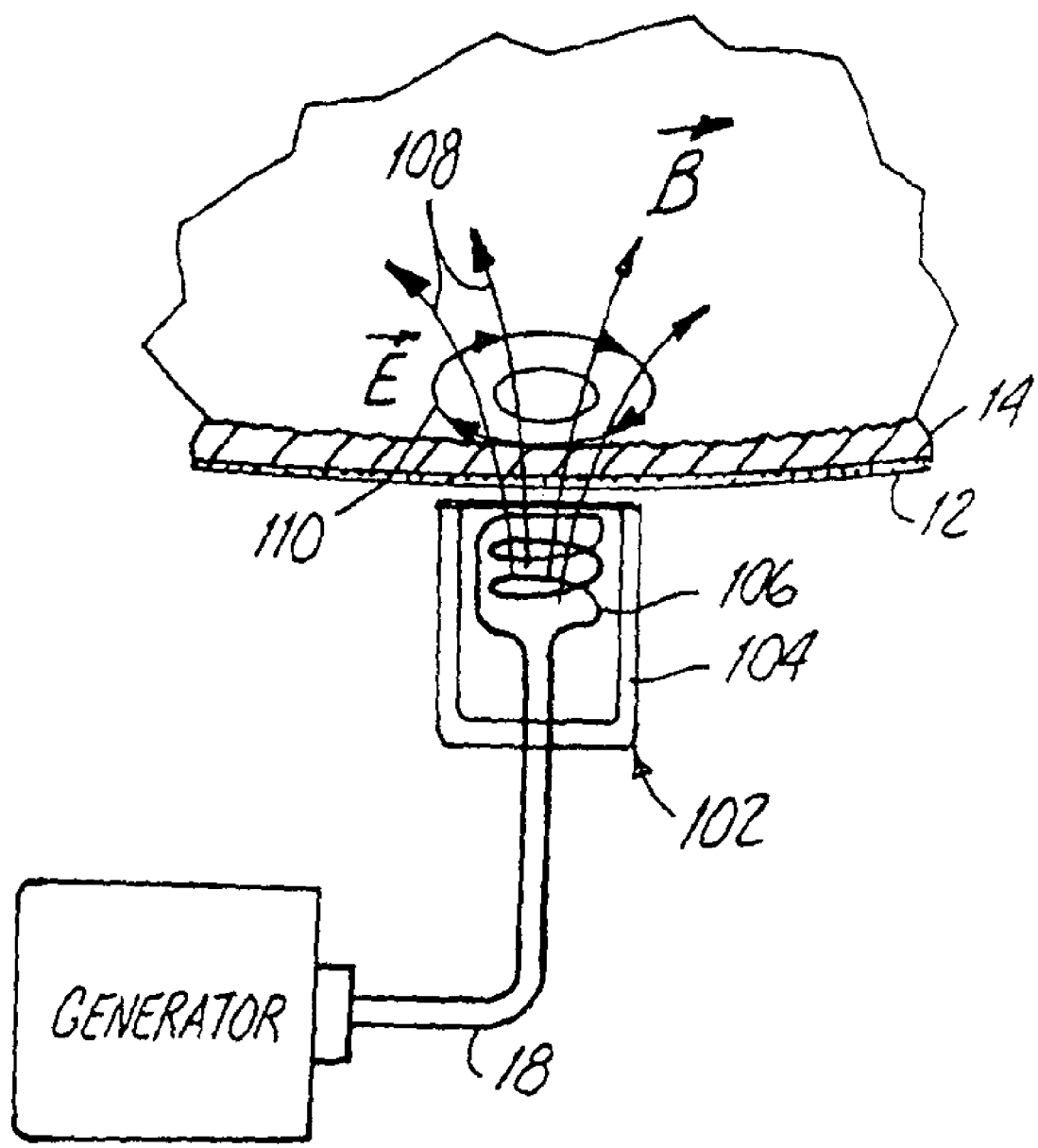
FIG. 5 is a schematic illustration of an apparatus for electroporation treatment for weight loss with electrodeless applicator.

FIG. 5 schematically illustrates another embodiment of the present invention including an electrodeless system 100. System 100 includes a high pulse current power supply 16 and an appropriate electrical connector 18 extending to an applicator 102. Applicator 102 comprises a housing 104 and an electromagnetic coil 106 disposed therein. Coil 106 generates a magnetic field 108 that is applied to the skin 12 and the subcutaneous tissues 14. The pulsed magnetic field 108 in the tissue exists only about 10 microseconds. The energy of rapidly changing magnetic field transforms into a curl electric field 110, which creates eddy currents in tissue and provides the electroporation treatment for killing the fat cells in the tissue 14. Preferably, the curl electric field generated in the subcutaneous tissue is in the range of 30 to 50 Volt/mm, and the duration of the pulses is 5 to 20 microseconds.

Figure 6:
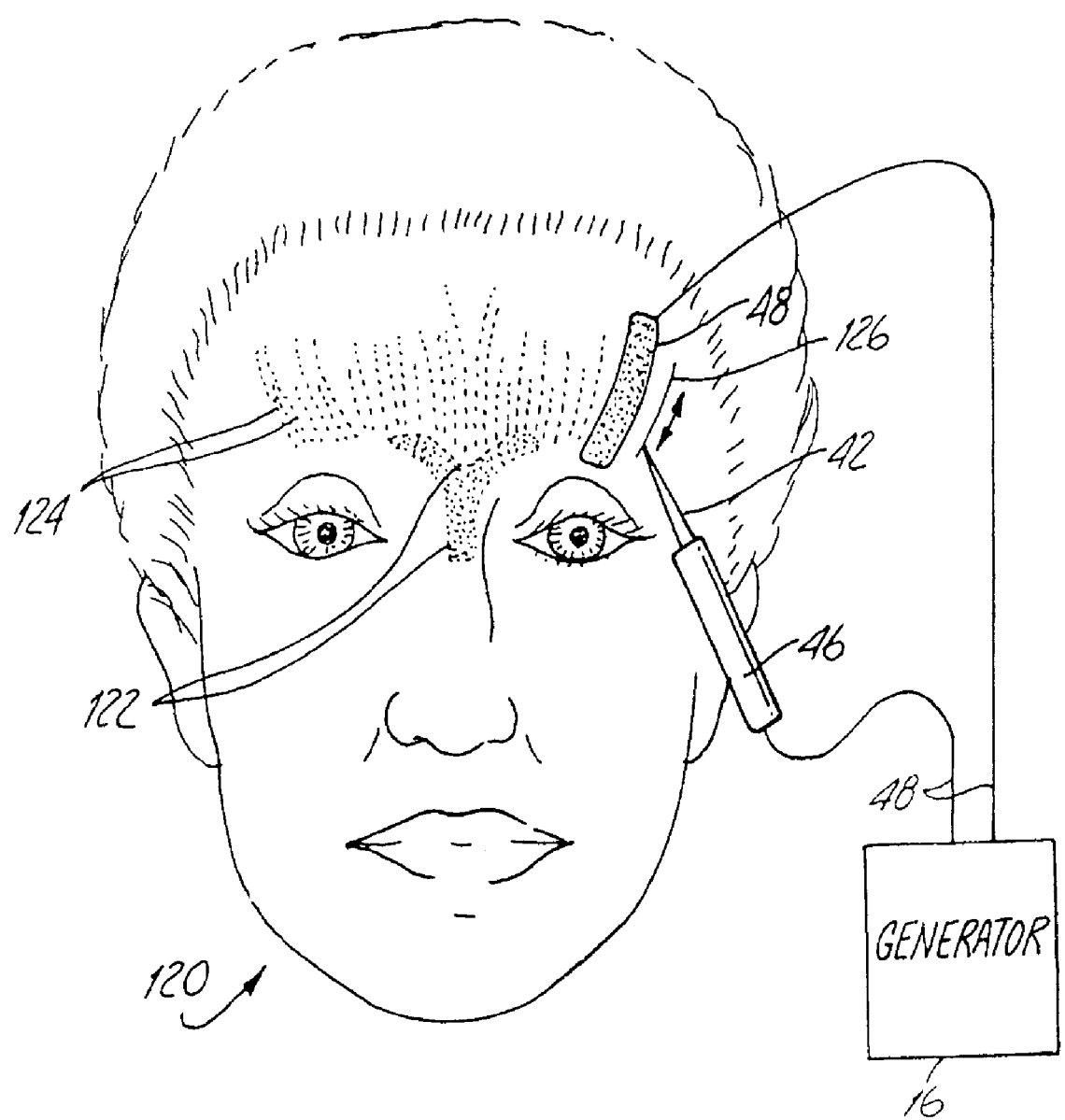
FIG. 6 is a frontal view of a human head with schematically shown electroporation treatment for removal of the forehead wrinkles and glabellar frown lines.

FIG. 6 schematically illustrates a frontal view of human head 120 with glabellar frown lines 122 and forehead wrinkles 124. An embodiment of the present invention Such as system 40 is shown in application. Electrode 44 is shown applied to the forehead and the needle electrode 42 is moved over the skin where treatment is desired. Moving the electrode tip along the skin creates a line of necrotic subcutaneous fat cells, which later are metabolized by the body. An exemplary line of treatment 126 is shown in the Figure. Multiple applications of the electrode along predetermined lines on the face or neck create shrinkage of the skin and the subcutaneous fat volume underlying the treated area.

Figure 7:
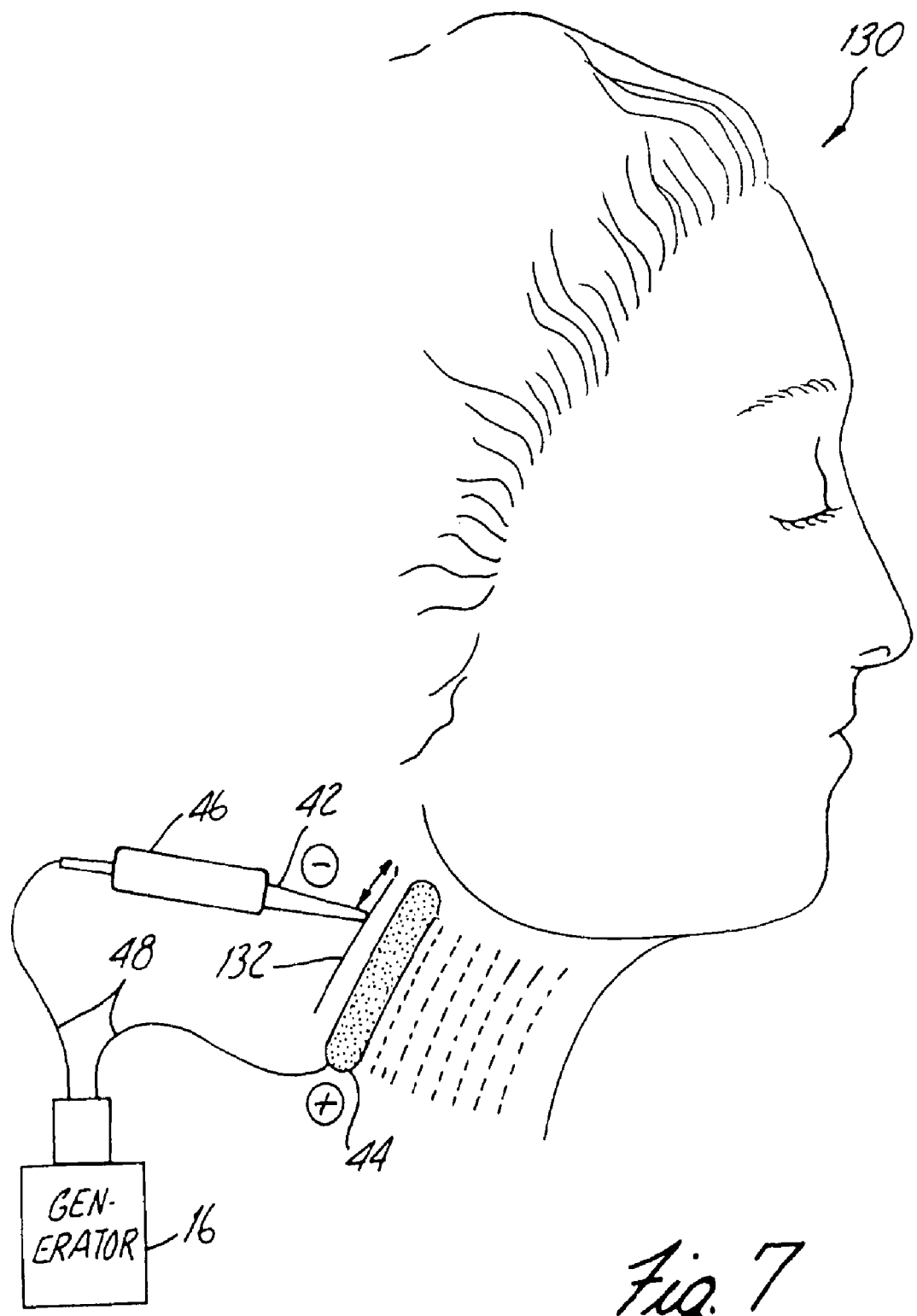
FIG. 7 is a lateral view of a human head with schematically shown electroporation treatment for a neck lift.

FIG. 7 depicts a lateral view of a human head 130 during a neck lift electroporation procedure using an electroporation system in accord with the present invention such as system 40. The figure illustrates an exemplary line of electroporation treatment 132.

The present invention having thus been described, other modifications, alterations, or substitutions may now suggest themselves to those skilled in the art, all of which are within the spirit and scope of the present invention. It is therefore intended that the present invention be limited only by the scope of the attached claims below.

What is claimed is:

1. A method of treating a living human body by destroying tissue cells, comprising:
   positioning one or more electrodes near a target area containing tissue cells to be killed in the living human body; and
   treating the living human body by applying electrical pulses through the positioned one or more electrodes in an amount above an upper limit of electroporation to irreversibly open pores in membranes of the tissue cells in the target area, thereby killing the tissue cells in the target area.

2. The method according to claim 1, wherein:
   the step of applying electrical pulses includes applying the electrical pulses between a needle-like electrode and a flat electrode.

3. The method according to claim 2, wherein:
   the step of applying includes applying the electrical pulses between the needle-like electrode having a first polarity and the flat electrode having a second polarity different from the first polarity.

4. The method according to claim 1, wherein, the one or more electrodes comprise an array of electrodes and wherein the step of positioning includes positioning the array of electrodes near the target area.

5. The method according to claim 1, wherein:
   the step of positioning includes positioning the one or more electrodes near a target area containing fat tissue cells; and
   the step of applying includes applying the electrical pulses in the amount above the upper limit of electroporation to irreversibly open pores in membranes of the fat tissue cells.

6. The method according to claim 1, wherein the step of applying includes applying electrical pulses whose amplitude is in a range of 20 Volt/mm and 2000 Volt/mm.

7. The method according to claim 1, wherein the step of applying includes applying electrical pulses whose amplitude is above 20 Volt/mm.

8. The method according to claim 1, wherein the step of applying includes applying electrical pulses whose duration is in a range of 10 microseconds and 100 milliseconds.

9. The method according to claim 1, wherein the step of applying includes applying electrical pulses whose amplitude is in a range of 20 Volt/mm and 2000 Volt/mm and whose duration is in a range of 10 microseconds and 100 milliseconds.

10. The method according to claim 1, wherein:
    the one or more electrodes include an electromagnetic coil; and
    the step of applying an electric field includes generating one or more magnetic pulses through the electromagnetic coil.

11. A method of treating a living human body by destroying tissue cells, comprising:
    positioning an electric field applicator near a target area containing tissue cells to be killed in the living human body; and
    applying an electric field through the positioned electric field applicator in an amount above an upper limit of electroporation to irreversibly open pores in membranes of the tissue cells to treat the living human body, thereby causing death of the tissue cells.

12. The method according to claim 11, wherein:
    the electric field applicator includes first and second electrodes;
    the step of positioning includes positioning the first and second electrodes near the target area; and
    the step of applying an electric field includes applying electrical pulses between the first and second electrodes.

13. The method according to claim 12, wherein:
    the first electrode is a needle-like electrode and the second electrode is a flat electrode; and
    the step of applying an electric field includes applying the electrical pulses between the needle-like electrode and the flat electrode.

14. The method according to claim 12, wherein:
    the first electrode is an electrode having a first polarity and the second electrode is an electrode having a second polarity different from the first polarity; and
    the step of applying includes applying the electrical pulses between the first electrode and the second electrode.

15. The method according to claim 11, wherein the step of positioning includes positioning an array of electrodes near the target area.

16. The method according to claim 11, wherein:
    the step of positioning includes positioning at least one electrode near a target area containing fat tissue cells; and
    the step of applying an electric field includes applying the electric field in the amount above the upper limit of electroporation to irreversibly open pores in membranes of the fat tissue cells.

17. The method according to claim 11, wherein the step of applying includes applying an electrical pulse whose amplitude is in a range of 20 Volt/mm and 2000 Volt/mm.

18. The method according to claim 11, wherein the step of applying includes applying an electrical pulse whose amplitude is above 20 Volt/mm.

19. The method according to claim 11, wherein the step of applying includes applying an electrical pulse whose duration is in a range of 10 microseconds and 100 milliseconds.

20. The method according to claim 11, wherein the step of applying includes applying an electrical pulse whose amplitude is in a range of 20 Volt/mm and 2000 Volt/mm and whose duration is in a range of 10 microseconds and 100 milliseconds.

21. The method according to claim 11, wherein:
the electric field applicator includes an electromagnetic coil; and
the step of applying an electric field includes generating one or more magnetic pulses through the electromagnetic coil.

* * * * *